| United States Patent [19] | [11] Patent Number: 4,788,351 |
|---|---|
| Takakuwa et al. | [45] Date of Patent: Nov. 29, 1988 |

[54] PROCESS FOR THE PRODUCTION OF 2,3-DICHLORO-1-PROPANOL

[75] Inventors: Sadao Takakuwa, Suita; Tetsuya Nakada; Keishiro Nagao, both of Amagasaki, all of Japan

[73] Assignee: Osaka Soda Co., Ltd., Osaka, Japan

[21] Appl. No.: 83,190

[22] Filed: Aug. 10, 1987

[30] Foreign Application Priority Data

Jul. 18, 1985 [JP] Japan .................. 60-158790
Jul. 26, 1985 [JP] Japan .................. 60-166320

[51] Int. Cl.$^4$ ............................. C07C 24/62
[52] U.S. Cl. ................................... 568/848
[58] Field of Search ......................... 568/848

[56] References Cited

U.S. PATENT DOCUMENTS 3,823,193  7/1974  Fernholz et al. .
4,634,784  1/1987  Nagato et al. .

FOREIGN PATENT DOCUMENTS 17206   1/1962  Japan .
18207  11/1973  Japan .
026243  7/1985  Japan .................. 568/848
60054   3/1986  Japan .
019544  1/1987  Japan .................. 568/848

*Primary Examiner*—Howard T. Mars
*Attorney, Agent, or Firm*—Wegner & Bretschneider

[57] ABSTRACT

Improved process for the production of 2,3-dichloro-1-propanol in high yield by chlorinating allyl alcohol with chlorine, which is characteristic in that the chlorination reaction proceeds by introducing simultaneously allyl alcohol and chlorine gas and optionally hydrogen chloride gas into the reaction system containing aqueous hydrochloric acid without necessity of extreme cooling and/or pressure.

6 Claims, No Drawings

PROCESS FOR THE PRODUCTION OF 2,3-DICHLORO-1-PROPANOL

This invention relates to an improved process for the production of 2,3-dichloro-1-propanol, more particularly, to an industrial process for the production of 2,3-dichloro-1-propanol by chlorinating allyl alcohol with chlorine, which is characteristic in that allyl alcohol and chlorine gas and optionally hydrogen chloride gas are simultaneously added to the reaction system containing aqueous conc. hydrochloric acid in a batch system or in a continuous system.

Prior Art

It is well known that 2,3-dichloro-1-propanol is very useful as a material for the production of glycerin and glycidol, or as an intermediate for the production of epichlorohydrin which is useful as a material for the production of epoxy resins, synthetic rubbers, etc.

Various processes have hitherto been known for the production of 2,3-dichloro-1-propanol. For example, it has been produced by chlorinating allyl alcohol with chlorine gas in carbon disulfide or without using any solvent, but these processes give the desired product in very low yield such as 20 to 40%.

It has recently been found that the low yield of the product in the above processes is largely due to some side reactions, e.g. oxidation of allyl alcohol to acrolein by chlorine, and further that these side reactions can be suppressed by the presence of hydrogen chloride. For example, it is known that the compound can be prepared in high yield by dissolving allyl alcohol in an organic solvent, saturating the solution with hydrogen chloride and then introducing chlorine gas thereto [cf. Japanese Patent First Publication (Kokai) No. 1361/1971 (=U.S. Pat. No. 3,823,193), and Japanese Patent Second Publication (Kokoku) No. 18207/1973]. However, these processes have some problems, such as loss of the product and the solvent during separation of the product from the solvent and hydrogen chloride and purification of the product by distillation.

There are also known processes without using any organic solvent by introducing chlorine gas into aqueous conc. hydrochloric acid wherein allyl alcohol is dissolved [cf. Japanese Patent Second Publication (Kokoku) No. 17206/1962, and Japanese Patent Second Publication (Kokoku) No. 60054/1986]. In the process disclosed in Japanese Patent Second Publication No. 17206/1962, a commercially available conc. hydrochloric acid can be used, which is advantageous from the industrial viewpoint, but this process is still unfavorable because of the low yield of the product (i.e. 50 to 70% yield). Besides, in the process disclosed in Japanese Patent Second Publication No. 60054/1986, the hydrochloric acid solution should be in such a high concentration as 50 to 75% by weight, and for such a purpose, hydrogen chloride gas must be introduced into the aqueous allyl alcohol solution prior to the chlorination, which requires disadvantageously an additional step. Moreover, in this process, the reaction should be carried out at a lower temperature and/or under pressure in order to keep the high concentration of hydrochloric acid, which requires disadvantagenously a specific expensive apparatus. Thus, this process is not necessarily preferable for the production of the compound on industrial scale.

It is also known in Japanese Patent First Publication (Kokai) No. 258171/1985 (=U.S. Pat. No. 4,634,784) that 2,3-dichloro-1-propanol is prepared by reacting allyl alcohol with chlorine in aqueous hydrochloric acid having a concentration of 45 to 70% by weight at a lower temperature and/or under pressure, and the 2,3-dichloro-1-propanol thus prepared is converted into epichlorohydrin in several steps. This process also requires a high concentration of hydrochloric acid and should be carried out at a lower temperature and/or under pressure, and hence, the same problems as mentioned above are included.

BRIEF DESCRIPTION OF THE INVENTION

The present inventors have intensively studied to improve these known processes in order to produce the desired 2,3-dichloro-1-propanol in higher yield without such problems as in these known processes, and have now found that the object can be achieved by supplying simultaneously the starting materials (allyl alcohol, chlorine gas and preferably further hydrogen chloride gas) into a reaction system containing aqueous hydrochloric acid, by which it is required neither to use very high concentration of hydrochloric acid nor to carry out the reaction at a very low temperature and/or under pressure, and hence, this process is very advantageous for the production of the desired compound on industrial scale.

An object of the invention is to provide an improved process for the production of 2,3-dichloro-1-propanol in high yield by a simple procedure using a commercially available hydrochloric acid. Another object of the invention is to provide a process for the production of 2,3-dichloro-1-propanol without using any specific pressure vessel. These and other objects and advantages of the invention will be apparent to those skilled in the art from the following description.

DETAILED DESCRIPTION OF THE INVENTION

The process for the production of 2,3-dichloro-1-propanol of this invention comprises introducing simultaneously allyl alcohol and chlorine gas and preferably further hydrogen chloride gas into the solvent (aqueous hydrochloric acid having a concentration of 25 to 40% by weight), whereby subjecting to the chlorination reaction of allyl alcohol.

In the chlorination of allyl alcohol in aqueous hydrochloric acid, there is generally possibility of occurrence of the following side reactions:

(1) production of allyl chloride by reaction of allyl alcohol with hydrochloric acid, (2) production of condensation products of allyl alcohol with chloronium ion which is an intermediate of the chlorination reaction, and (3) production of condensation products of the above chloronium ion with 2,3-dichloro-1-propanol produced.

In order to increase the yield of the desired product, 2,3-dichloro-1-propanol, it is important to suppress the above side reactions. From this viewpoint, the present inventors have studied on the conditions suitable for suppressing the side reactions and have found that it is necessary, (i) to keep the concentration of allyl alcohol in the reaction mixture as small as possible and thereby to make the contact time of allyl alcohol with hydrochloric acid as short as possible in order to suppress the side reaction (1), and (ii) to lower the nucleophilicity of allyl alcohol or 2,3-dichloro-1-propanol to chloronium ion in the reaction mixture in order to suppress the side reactions (2) and (3).

Based upon the above findings, it has newly been found that, by introducing simultaneously allyl alcohol and chlorine gas into the reaction system containing aqueous hydrochloric acid through separate inlets and preferably by supplying also simultaneously hydrogen chloride gas in order to keep the desired concentration of hydrochloric acid in the reaction system, the undesirable side reactions are effectively suppressed and hence the reaction results in extremely high yield of the desired product. According to this process, allyl alcohol is immediately chlorinated with chlorine introduced simultaneously because the reaction of allyl alcohol with chlorine proceeds very rapidly in aqueous hydrochloric acid, and hence, the contact time of allyl alcohol with hydrochloric acid and chloronium ion becomes negligibly small, by which the side reactions (1) and (2) as mentioned above can be minimized. In fact, according to the process of this invention, the by-products such as allyl chloride or derivatives thereof are less than 1% or in preferred embodiment less than 0.5%. Moreover, in the feature of simultaneous supplying of hydrogen chloride gas, even though the aqueous hydrochloric acid is diluted with 2,3-dichloro-1-propanol produced, the desired concentration of hydrochloric acid (i.e. in saturated state) can be kept by supplying hydrogen chloride gas, and thereby, the nucleophilicity of 2,3-dichloro-1-propanol to chloronium ion is reduced, and hence the above-mentioned side reaction (3) can significantly be suppressed even in the presence of a comparatively high concentration of 2,3-dichloro-1-propanol in the reaction system.

As the solvent, a commercially available conc. hydrochloric acid can well be used. The aqueous hydrochloric acid used as the solvent in this invention has usually a concentration of 25 to 40% by weight, preferably 30 to 40% by weight, more preferably 35 to 40% by weight. When the concentration of hydrochloric acid is lower than 25% by weight, the undesirable oxidation of allyl alcohol to acrolein is observed. Besides, as is mentioned hereinbefore, with progress of the reaction, the solvent is diluted with 2,3-dichloro-1-propanol produced, and hence, the concentration of hydrochloric acid in the reaction system is further decreased. In order to prevent such dilution during the reaction, it is preferable to supply hydrogen chloride gas. However, when hydrogen chloride gas is supplied to, the temperature of the reaction mixture raises owing to the heat from dissolution of hydrogen chloride as well as from exothermic reaction of the chlorination of allyl alcohol. Accordingly, when a too large amount of hydrogen chloride gas is supplied to, it is difficult to control the temperature of the reaction mixture, and extra enegy is required for cooling the reaction mixture. Moreover, when the concentration of hydrochloric acid in the solvent is lower at the initiation of reaction, it results in low yield of the product. From these viewpoints, it is preferable to use as a solvent aqueous hydrochloric acid having a concentration of not less than 25% by weight. On the other hand, when the solvent has a concentration of hydrochloric acid of more than 40% by weight, it is disadvantageously required to employ any means for increasing the concentration, such as a specific cooling device, a pressure vessel, etc.

The solvent, aqueous hydrochloric acid is used in an amount of not less than two times by weight, preferably 2 to 8 times by weight, more preferably 3 to 5 times by weight, as much as the total amount of allyl alcohol to be introduced thereto. When the amount of the solvent is less than two times by weight, the side reaction (3) as mentioned hereinbefore by the reaction of 2,3-dichloro-1-propanol with chloronium ion disadvantageously increases remarkably.

The allyl alcohol and chlorine gas are introduced in about equimolar amount, usually 1:1 to 1:1.01 by mole. These are preferably introduced through separate introducing ducts. When a large excess amount of allyl alcohol and/or chlorine gas is introduced, it induces disadvantageously underisable side reactions. The allyl alcohol and chlorine gas are introduced at a rate of 0.01 to 50 mole/L·hr (L = liter of initial solvent), preferably 0.1 to 20 mole/L·hr, in a batch system or in a continuous system. In case of supplying further hydrogen chloride gas, it is supplied to in an amount of 0.5 to 3 times by mole, preferably 1 to 1.5 times by mole, as much as the amount of allyl alcohol. The reaction mixture can be kept being saturated with hydrochloric acid, and even though hydrogen chloride gas is continuously supplied to the reaction system, the concentration of hydrochloric acid in the reaction system does not over that of conc. hydrochloric acid (e.g. about 45% by weight at 0° C.) because of the poor solubility of hydrogen chloride in 2,3-dichloro-1-propanol produced. It is also apparent that supply of large excess of hydrogen chloride gas is fruitless, because the reaction mixture is saturated with it. The hydrogen chloride gas may be introduced into the reaction system through an independent introducing duct, but is preferably introduced through the same duct as that of chlorine gas as a mixture of hydrogen chloride gas and chlorine gas.

The reaction of this invention is preferably carried out with agitation. It is preferable to control the reaction temperature as low as possible in order to increase the yield of the product, but from the industrial viewpoint, in order to keep low viscosity of the reaction mixture or to save energy for cooling, it is preferable to carry out the reaction at a temperature of from −5° to 10° C. under atmospheric pressure. The reaction may be done under light, but is preferably carried out with protection from light in order to increase the yield of the product.

The product, 2,3-dichloro-1-popanol, can be isolated from the reaction mixture by a conventional method, for example, by neutralizing the reaction mixture with a basic compound (e.g. sodium hydroxide, calcium hydroxide, etc.) or purging at least a portion of hydrogen chloride gas with an inert gas (e.g. nitrogen gas), and then subjecting the mixture to distillation. When the product is used as an intermediate for the other products such as epichlorohydrin, the reaction mixture containing 2,3-dichloro-1-propanol may be subjected to the subsequent reactions after partially removing hydrochloric acid therefrom, without isolation of the product.

The process of this invention can be carried out by using a commercially available aqueous hydrochloric acid as a solvent by a simple procedure without necessity of use of any specific apparatus. Moreover, the reaction proceeds without undesirable lowering of the concentration of hydrochloric acid in the solvent when hydrogen chloride gas is supplied to simultaneously together with the starting materials, and hence, the undesirable side reactions can effectively be prevented and the desired product can be obtained in very high yield.

The present invention is illustrated by the following Examples and Reference Examples, but should not be construed to be limited thereto.

EXAMPLE 1

A reaction vessel provided with an agitator is charged with 40 wt. % aqueous hydrochloric acid (110 g, 1.2 mole as HCl), and thereto are added with agitation allyl alcohol (23.4 g, 0.4 mole) and chlorine gas (28.8 g, 0.4 mole) through separate introducing ducts at a rate of equimolar amount over a period of time of 45 minutes at −5° C. under atmospheric pressure and under protection from light.

After the reaction is completed, the reaction mixture is directly analyzed by gas chromatography (hereinafter, abbreviated as GC method) with a column packed with OV-225 (5%)/Chromosolve W AW-DMCS using biphenyl as an internal standard. The yield of 2,3-dichloro-1-propanol is 95.0%.

EXAMPLE 2

In the same manner as described in Example 1 except that 35 wt. % aqueous hydrochloric acid (115 g, 1.1 mole as HCl) is used and the reaction temperature is maintained at 0° C., the reaction is carried out, and the reaction mixture is analyzed by GC method likewise. The desired 2,3-dichloro-1-propanol is produced in an yield of 90.2%.

EXAMPLE 3

In the same manner as described in Example 1 except that 30 wt. % aqueous hydrochloric acid (89 g, 0.73 mole as HCl) is used and the reaction temperature is maintained at 10° C., the reaction is carried out. The desired 2,3-dichloro-1-propanol is produced in an yield of 85.6%.

REFERENCE EXAMPLE 1

The same reaction vessel as used in Example 1 is charged with 20 wt. % aqueous hydrochloric acid (54.5 g, 0.3 mole as HCl), and thereto are added with agitation allyl alcohol (5.9 g, 0.1 mole) and chlorine gas (7.0 g, 0.1 mole) through separate introducing ducts at a rate of equimolar amount over a period of time of 45 minutes at 0° C. under atmospheric pressure and under protection from light.

After the reaction is completed, the reaction mixture is directly analyzed by GC method likewise. The yield of 2,3-dichloro-1-propanol is 58.6%.

REFERENCE EXAMPLE 2

The same reaction vessel as used in Example 1 is charged with 35 wt. % aqueous hydrochloric acid (30 g, 0.29 mole as HCl) and allyl alcohol (11.6 g, 0.2 mole), and thereto is added with agitation chlorine gas (14.2 g, 0.2 mole) over a period of time of 45 minutes at 0° C. under atmospheric pressure and under protection from light.

After the reaction is completed, the reaction mixture is directly analyzed by GC method. The yield of 2,3-dichloro-1-propanol is 72.0%.

EXAMPLE 4

A reaction vessel provided with an agitator is charged with 37 wt. % aqueous hydrochloric acid (110 g, 1.1 mole as HCl), and thereto are added with agitation allyl alcohol (23.2 g, 0.4 mole) and a mixture of chlorine gas (28.8 g, 0.4 mole) and hydrogen chloride gas (22 g, 0.6 mole) through separate introducing ducts at a rate of equimolar amount of the allyl alcohol and chlorine gas over a period of time of 45 minutes at 0° C. under atmospheric pressure and under protection from light.

After the reaction is completed, excess amount of hydrogen chloride gas is purged by blowing therein nitrogen gas, and then the reaction mixture is directly analyzed by GC method. The yield of 2,3-dichloro-1-propanol is 98.1%.

EXAMPLE 5

The same reaction vessel as used in Example 4 is charged with 30 wt. % aqueous hydrochloric acid (150 g, 1.2 mole as HCl), and thereto are added with agitation allyl alcohol (23.5 g, 0.4 mole) and a mixture of chlorine gas (28.8 g, 0.4 mole) and hydrogen chloride gas (43.8 g, 1.2 mole) through separate introducing ducts at a rate of equimolar amount of the allyl alcohol and chlorine gas over a period of time of 45 minutes at 0° C. under atmospheric pressure and under protection from light.

After the reaction is completed, the reaction mixture is treated in the same manner as in Example 4 and is analyzed by GC method. The yield of 2,3-dichloro-1-propanol is 95.1%.

EXAMPLE 6

The same reaction vessel as used in Example 4 is charged with 40 wt. % aqueous hydrochloric acid (50 g, 0.54 mole as HCl), and thereto are added with agitation allyl alcohol (23.4 g, 0.4 mole) and a mixture of chlorine gas (28.8 g, 0.4 mole) and hydrogen chloride gas (7.3 g, 0.2 mole) through separate introducing ducts at a rate of equimolar amount of the allyl alcohol and chlorine gas over a period of time of 45 minutes at −5° C. under atmospheric pressure and under protection from light.

After the reaction is completed, the reaction mixture is treated in the same manner as in Example 4 and is analyzed by GC method. The yield of 2,3-dichloro-1-propanol is 98.3%.

What is claimed is:

1. In a process for the production of 2,3-dichloro-1-propanol comprising reacting allyl alcohol and chlorine gas in aqueous hydrochloric acid, the improvement comprises using an aqueous solution of hydrochloric acid having a concentration of 25 to 40% by weight and carrying out the reaction of allyl alcohol and chlorine gas by supplying allyl alcohol and chlorine gas simultaneously to the reaction system.

2. The process according to claim 1, wherein hydrogen chloride gas is also simultaneously supplied.

3. The process according to claim 1, wherein the allyl alcohol and chlorine gas are introduced in a ratio of 1:1 to 1:1.01 by mole.

4. The process according to claim 1, wherein the allyl alcohol and chlorine gas are introduced at a rate of 0.01 to 50 mole/L·hr, respectively.

5. The process according to claim 1, wherein the aqueous solution of hydrochloric acid has a concentration of 30 to 40% by weight.

6. The process according to claim 2, wherein the hydrogen chloride gas is supplied in an amount of 0.5 to 3 times by mole as much as the amount of allyl alcohol.

* * * * *